United States Patent [19]

Peyman et al.

[11] 4,073,015
[45] Feb. 14, 1978

[54] ARTIFICIAL INTRAOCULAR LENS ATTACHMENT

[76] Inventors: Gholam A. Peyman, 1044 N. Oak Park Ave.; Jeffrey E. Koziol, 1213 N. Lombard St., both of Oak Park, Ill. 60300

[21] Appl. No.: 762,007

[22] Filed: Jan. 24, 1977

Related U.S. Application Data

[63] Continuation-in-part of Ser. No. 684,248, May 7, 1976, abandoned.

[51] Int. Cl.² .......................... A61F 1/16; A61F 1/24
[52] U.S. Cl. ...................................................... 3/13
[58] Field of Search ................................. 3/13, 1, 1.9

[56] References Cited

U.S. PATENT DOCUMENTS

| | | | |
|---|---|---|---|
| 2,714,721 | 8/1955 | Stone | 3/1 |
| 3,673,616 | 7/1972 | Fedorov et al. | 3/13 |
| 3,783,454 | 1/1974 | Sausse et al. | 3/1 |
| 3,906,551 | 9/1975 | Otter | 3/13 |
| 3,909,852 | 10/1975 | Homsy | 3/1.9 |
| 3,971,073 | 7/1976 | Richards et al. | 3/13 |

*Primary Examiner*—Ronald L. Frinks
*Attorney, Agent, or Firm*—Ray E. Snyder

[57] ABSTRACT

An improved intraocular lens mounting system for an Iris Clip type of lens. The lens has haptical portions extending laterally from the edges of the lens transversely to the optic axis of the lens. Fibrous material such as Dacron is attached to the outer edges of the haptical portions and provide bases into which the tissue of the iris can grow so as to form a firm anchor for the lens. The lens may also have two or more attached loops projecting in a plane generally parallel to the plane of the lens and to the haptical portions. The loops may be coated or encased in a sleeve of fibrous material and hold the lens in place with respect to the iris until tissue growth into the Dacron material is accomplished.

7 Claims, 14 Drawing Figures

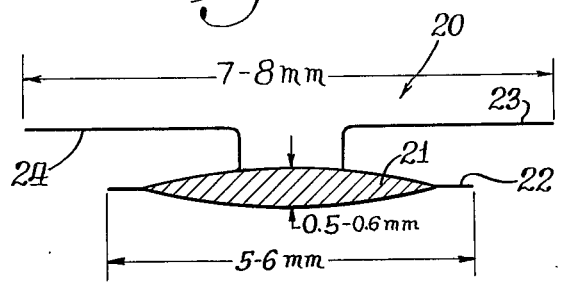
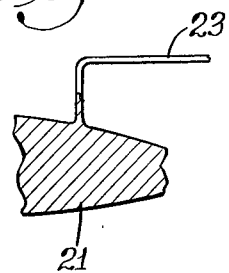
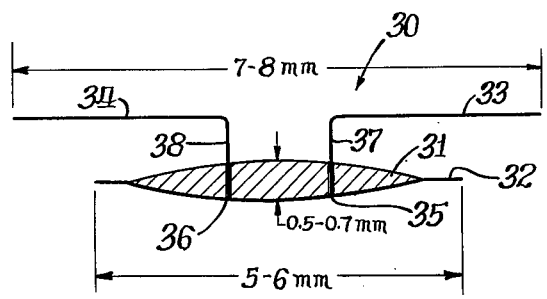
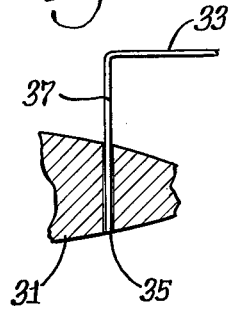
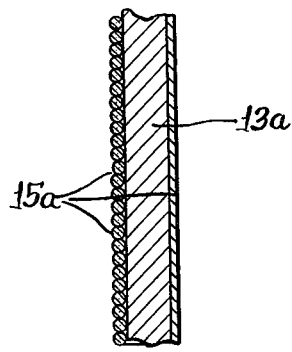

ARTIFICIAL INTRAOCULAR LENS ATTACHMENT

CROSS-REFERENCE TO RELATED APPLICATION

This application is a Continuation-in-Part of our earlier filed pending application, Ser. No. 684,248 filed May 7, 1976 and now abandoned.

BACKGROUND OF THE INVENTION

1. Field of the Invention.

This invention relates generally to Artificial Body Members, and more specifically to artificial intraocular lenses for implanting or mounting within the eye.

2. Description of the Prior Art.

The concept of the use of intraocular lenses for the correction of aphakia has a long history. The actual practice of implanting lenses is relatively recent. Much of the pioneering work was performed by Harold Ridley in London and by Binkhorst in the Netherlands. A comprehensive history of the development and results of the intraocular implant lens is presented in a thesis by Marcel Eugene Nordlohne and reproduced in Documenta Ophthalmologica, Vol. 38, Issue 1, Dec. 16, 1974.

A variety of intraocular lenses of the general type of the present invention are also described in the patent literature. These include the patents to:

Lieb, W. A.   2,834,023   ANTERIOR CHAMBER LENSES FOR REFRACTIVE CORRECTION OF APHAKIA Deitrick, R. E.   3,711,870   ARTIFICIAL LENS IMPLANT Fedorov, S. N.   3,673,616   ARTIFICIAL ANTERIOR CHAMBER LENS Flom, L.   3,866,249   POSTERIOR CHAMBER ARTIFICIAL INTRAOCULAR LENS Otter, K.   3,906,551   ARTIFICIAL INTRAOCULAR LENS SYSTEM Potthast, E. W.   3,913,148   INTRAOCULAR LENS APPARATUS Most of the patents listed above are addressed to the problem of mounting the lens within the eye so that it can perform its intended function with a minimum of trauma to the eye. This has been a major problem from the earliest of times. An early report by Schiferli in 1795 described an attempt by Casaamata to introduce a glass lens into the eye after a cataract operation. The lens immediately slid back towards the fundus of the eye.

The problem of mounting a biologically tolerable lens has continued to plague the development of the implant practice. Previous lenses have relied on mechanical pressure fixation to hold the lens within the eye. Using this type of fixation requires a balance between the pressure necessary to stabilize the lens within the eye, holding it in place, and that amount of pressure that will cause tissue necrosis. Thus a lens cannot be mechanically fixed to ocular tissue with a great deal of pressure or the tissue will necrose and be damaged. All prior pupillary fixation lenses have thus erred on the side of being too loose and therefore require an additional fixation such as a suture or wire being placed through the lens.

SUMMARY OF THE INVENTION

This invention is directed to an improved means of mounting an intraocular lens so as to hold it in place permanently, and with no lasting irritation to the patient. The lens is made of acrylic, hydrogel, or other biologically tolerable lens material and is formed with laterally extending planar flanges or haptical portions. A woven or knitted fibrous material, such as Dacron, is attached to the outer perimeter of the haptical portions and provide sites into which tissue of the iris can grow so as to form a permanent anchor for the lens.

The lens mounting system may also include two or more attached loops projecting in a plane generally parallel to the plane of the lens and haptical portions. In some embodiments of the invention, the outer perimeter of the loops may be coated or encased in a sleeve of fibrous material. The loops serving to hold the lens in place with respect to the iris until tissue growth into the Dacron material is accomplished.

Alternative embodiments include a circular loop attached to the lens and disposed within the pupil of the iris, or two or more hooks attached to the perimeter of the haptical portions and adapted to engage the iris and hold the lens in place until tissue growth into the Dacron occurs. Such hooks preferably are made of an absorbable implantable surgical material which is absorbed by the body some time after attachment to the Dacron material has taken place.

BRIEF DESCRIPTION OF THE DRAWINGS

FIG. 5 is a sectional side view, similar to FIG. 2, with mounting loops molded integrally with the lens;

FIG. 5A is an enlarged fragmentary view, taken from FIG. 5, showing details of the structure;

FIG. 6 is a sectional side view, similar to FIG. 5, showing a lens structure with holes drilled therethrough and arms or loops of the same material as the lens being attached or welded thereto;

FIG. 6A is an enlarged fragmentary view, taken from FIG. 6, showing details of the joinder;

FIG. 7 is an enlarged fragmentary view of a portion of an arm or loop with fibrous material attached;

DETAILED DESCRIPTION OF THE DRAWINGS

Figure 1:
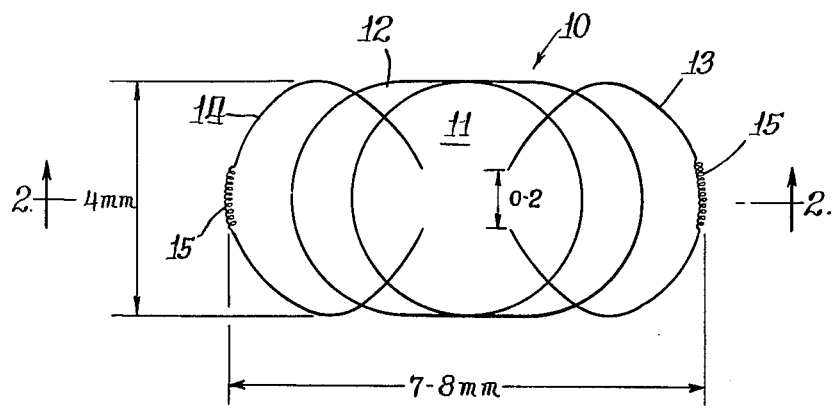
FIG. 1 is a plan view of the improved lens system of the present invention.
Figure 2:
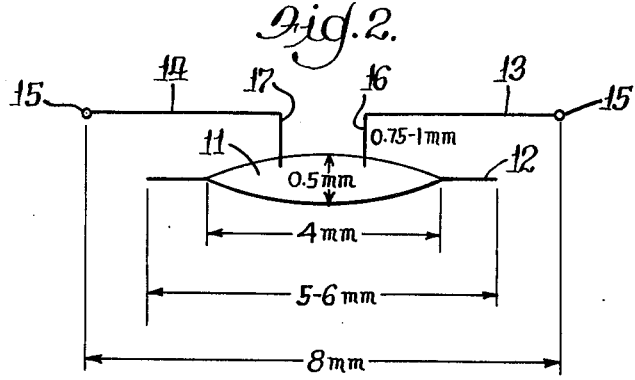
FIG. 2 is a sectional side view taken on line 2—2 of FIG. 1.

The improved lens structure and lens mounting system of the present invention is illustrated in FIGS. 1 & 2 and is designated generally by the numeral 10. The system 10 comprises a lens body 11 formed with an integral haptical portion 12, and attached loops 13 and 14. The outermost extremities of the loops 13 and 14 are coated or encased with fibrous sleeves 15, preferably made of Dacron polyester. The preferred dimensions for the lens system 10 are also set forth in the figures.

The lens body 11 is shown as double-convex, although it is to be understood that a plano-convex or concavo-convex lens would work equally well in this application, provided it had the same required focal length.

Figure 3:
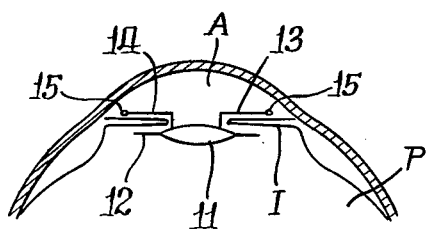
FIG. 3 is a fragmentary sectional view of an eye showing a posterior chamber mounting of the lens of FIG. 1.
Figure 4:
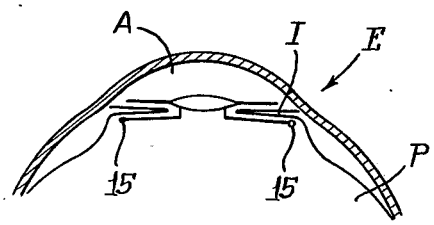
FIG. 4 is a view similar to FIG. 3 with an anterior chamber mounting of the lens.

For an anterior chamber mounting of the lens system 10, as shown in FIG. 4, the lens body 11 should have a standard power in aqueous of about +19.5D, with a range of powers above and below this figure for individual cases. For a posterior chamber mounting, as shown in FIG. 3, the power of the lens 11 should be slightly greater.

The lens body 11 preferably is made of an acrylic type of material known as polymethylmethacrylate, or known under trade names as Perspex or Plexiglass. This type of material has been shown to be tolerated within the eye, with little or no irritation. The haptical portion 12 is a generally oval or elliptical planar surface of the same material and formed integrally with the lens body 11, lying within the plane of the lens body 11.

The loops 13 and 14 have perpendicular legs 16 & 17, respectively, which penetrate and are imbedded in the lens body 11. The points of penetration of the legs 16 & 17 are relatively near the central axis of the lens body 11. This is to allow the iris of the eye in which the lens system 10 is implanted to contract to substantially its minimum aperture without undue restriction. The legs 16 & 17 may be affixed by ultrasound penetration or other suitable means.

The loops 13 and 14 preferably are made of platinumiridium, which is a very inert metal alloy; however, other metal wires, or other non-metallic materials that are tolerated within the eye may also be used. It is desirable to minimize the overall weight of the lens system 10, so the loop structures 13 and 14 should be of the smallest diameter possible that will still provide the necessary strength and rigidity.

The sleeves 15 preferably are made of knitted or woven fibrous material, such as Dacron, and wound on the outer peripheries of the loops 13 and 14, or alternatively, the sleeves 15 may be placed on the loops 13 and 14 before the latter are affixed to the lens body 11.

The procedures for sterilizing the lens system 10 prior to implantation, and the surgical procedures for performing the operation, are described in the Nordlohne thesis cited above.

Referring now to FIG. 3, a fragmentary sectional view of an eye shows the lens system 10 mounted in the posterior chamber. The portion of the eye E shown has an anterior chamber A and a posterior chamber P. The two chambers are separated by an iris I and the lens system 10 is mounted in the location previously occupied by the crystalline lens. The pupillary opening in the iris I is expanded to admit the lens body 11 and haptical portion 12. The haptical portion 12 of the lens 11 lies behind the iris I in a plane generally parallel to the pupillary aperture. The loops 13 and 14 lie in front of the iris I and the sleeves 15 come into contact with the iris I. The iris is sandwiched between the haptical portion 12 and the loops 13 and 14 so that the lens 11 is held in its proper place. Medication is used to constrict the pupil against the legs 16 and 17 to properly center the lens system 10. In a matter of a few days, tissue of the iris in contact with the fibrous material 15, grows into this material, and thereby anchors the lens system 10 in place permanently.

The procedures for mounting the anterior chamber lens system 10, as shown in FIG. 4, are substantially the same as those described above for the posterior chamber. The pupillary aperture of the iris I is enlarged to admit the arms 13 and 14, and the lens body 11 and haptical portion 12 are oriented in a plane substantially parallel to the plane of the iris I. The lens body 11 and haptical portion 12 cover the pubillary opening, and the sleeves 15 on the arms 13 and 14 contact the tissue on the posterior surface of the iris I. Medication is added to contract the pupil, and the lens system 10 is held in place until tissue of the iris I grows into the fibrous sleeves 15.

Referring now to FIGS. 5 & 5A, there is illustrated a modified construction of a lens system 20. In this embodiment, the lens body 21, haptical portion 22, and arms 23 & 24 are molded as a single, integral unit. The dimensions of the integral structure 20 are substantially the same as those of the lens system 10.

The primary advantages of this modification are to simplify construction and eliminate some of the complexities of working with dissimilar materials. The methacrylate materials have been proven to be nontoxic in this environment, but the long term, and possible toxic, effects of some metal alloys are not completely established.

Another modification of the lens system 10 of FIG. 1 is illustrated in FIGS. 6 & 6A. In this latter embodiment a lens system 30 comprises a lens body 31, haptical portion 32, and arms 33 & 34. The arms 33 & 34 are formed in monofilament configuration of the same acrylic type of material as the lens body 31. The lens body 31 is drilled to form holes 35 & 36 to receive legs 37 & 38, respectively, of the arms 33 & 34. Once inserted in the holes 35 & 36, the legs 37 & 38 are bonded in place by any suitable technique, such as solar welding. This construction has the advantages of eliminating the problems of working with dissimilar materials, and simplifying the molding process by inserting the arms after the lens body 31 and haptical portion 32 has been molded. This latter structure 30, may also permit the controlled heat-setting of the loops 33 & 34 to ensure proper resilience for this application.

The lens bodies of the above described systems 10-30, may also be made of hydrophilic materials, such as are used in soft contact lenses. Such material may be monomers of the acrylate and methacrylate series formed into three-dimensional hydrogels. A comprehensive description of the soft contact lens materials is to be found in Chapter 1, entitled: "Polymeric aspects of soft contact lenses" by Kenneth F. O'Driscoll in a book entitled: "SOFT CONTACT LENS" published by the C. V. Mosby Co., St. L., 1972.

It is deemed important for the proper functioning of the present invention that the fibrous material 15 surrounding the outer perimeter of the loops adhere only to the iris. That is, it is important to avoid the inadvertent tissue growth into the fibrous material 15 by contact with the cornea or other part of the eye. To this end, the fragmentary view of FIG. 7 shows a short section of a loop with fibrous material on only one side — the side adapted to contact the iris when mounted. This can be accomplished by bonding the fibrous material to one side only, or by surrounding the outer surface of the loop and coating the non-functional side with an inert material. Another means of accomplishing the same result is to start with the fibrous material encircling the loop and heat fusing the fibers on the non-functional side.

Figure 8:
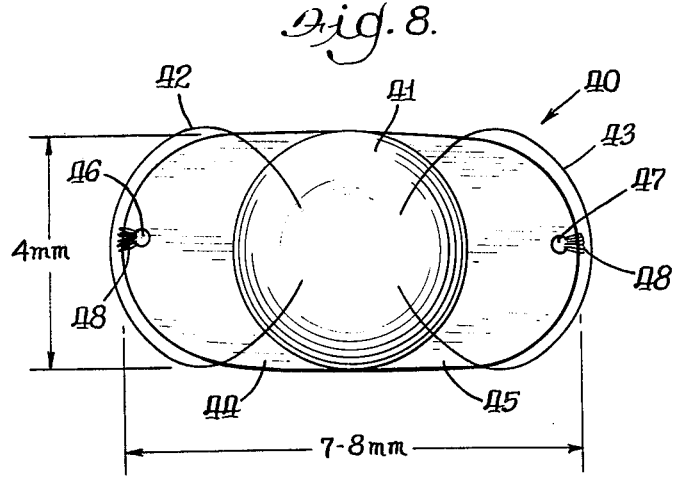
FIG. 8 is a plan view of a still further improved lens mounting system in which the fibrous material is attached to the haptical portions of the lens.

An additional alternative embodiment 40 of the invention is shown in FIG. 8. The lens system 40 comprises a lens body 41, loops 42 and 43, and expanded or elongated haptical portions 44 and 45. The outermost edges of the haptical portions 44 and 45 are formed with apertures 46 and 47, respectively, through which Dacron thread 48 is wound. The lens system 40 is intended for anterior chamber mounting with the loops 42 and 43 being inserted through the pupillary aperture of the iris and with the haptical portions 44 and 45 resting against the anterior surface of the iris. The lens system 40 is oriented so that the apertures 46 and 47 lie in a vertical plane for an erect patient. The iris is contracted by medication as previously described and the loops 42 and 43 hold the lens system 40 relatively fixed with respect to the iris until tissue of the iris can grow into the Dacron windings 48. Thereafter, primary support for holding the lens system 40 in place is by the adhesion of the Dacron material 48 to the iris.

Figure 9:
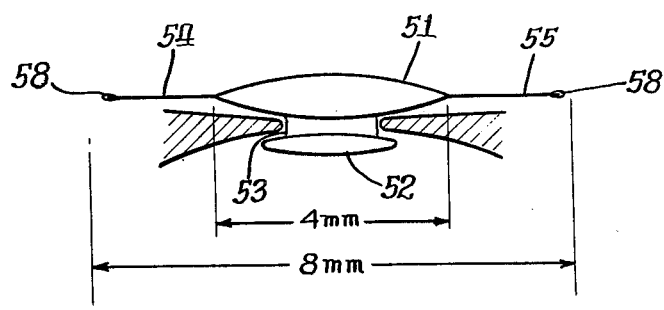
FIG. 9 is an alternative mounting system utilizing a circular loop in place of the laterally projecting loops for holding the lens in place.
Figure 10:
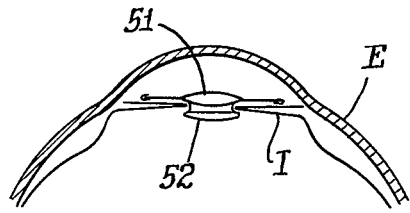
FIG. 10 is a fragmentary sectional view of an eye showing the anterior chamber mounting of the system of FIG. 9.

A further modification of the embodiment of FIG. 8 is shown in FIG. 9. In this embodiment 50, the lens body 51, haptical portions 54 and 55, apertures 56 and 57, and Dacron material 58 are substantially the same as in FIG. 8. The loops 42 and 43 are replaced by a circular ring 52 which is attached to the lens 51 by two or more supporting pins or wires 53. The ring 52 is inserted through the pupil and medication is added to contract the iris against the pins 53. The lens system 50 is held in place in the manner of a collar button until tissue growth into the Dacron material 58 is accomplished.

Figure 11:
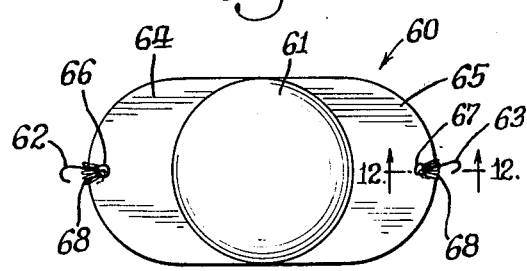
FIG. 11 is an alternative embodiment of the lens of FIG. 8 in which hooks are attached to the perimeter of the haptical portions for temporarily attaching the lens to the iris of an eye.
Figure 12:
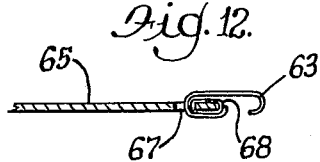
FIG. 12 is an enlarged fragmentary view of the haptical portion taken on line 12—12 of FIG. 11.

An additional and simplified modification of the embodiment of FIG. 8 is shown in FIGS. 11 and 12. This embodiment of a lens system 60 comprises a lens body 61, haptical portions 64 and 65, a pair of hooks 62 and 63 attached to the haptical portions 64 and 65, respectively, and Dacron material 68. The haptical portions 64 and 65 are formed with apertures 66 and 67, respectively, through which the Dacron material 68 is wound. The hooks 62 and 63 are also attached to the haptical portions 64 and 65 through the apertures 66 and 67.

The hooks 62 and 63 preferably are made of an absorbable suture material such as is made from fibrin, the protein formed by clotting blood. The lens body 61 is implanted in the anterior chamber of an eye over the pupil with the apertures 66 and 67 aligned in a vertical plane (for an erect patient). The hooks 62 and 63 engage the tissue of the iris and hold the Dacron material 68 in contact with the anterior surface of the iris. After tissue growth into the iris has taken place, the hooks 62 and 63 are no longer necessary and are absorbed.

We have found that the attachment of intraocular lenses by tissue growth of the iris into the fibrous Dacron material in the manner described herein makes an effective and permanent mounting with a minimum of trauma to the eye. The fact that tissue of the iris would grow into the Dacron as effectively as it does was unexpected because it is well known that a perforation of the iris does not heal itself.

The embodiments shown and described are by way of example and it is to be understood that many changes and modifications might be made thereto without departing from the spirit of the invention. The invention is not to be construed as limited to the embodiments shown and described, except in-so-far as the claims may be so limited.

We claim:

1. An artificial intraocular lens system adapted to be implanted within a living eye immediately adjacent the iris of the eye and comprising:
   a plastic optical lens portion formed with a laterally extending haptical portion from said lens portion; and
   attachment means including a biologically tolerable fibrous material mounted on the outer periphery of said haptical portion and adapted to contact the iris of the eye so that tissue growth of the iris into the fibrous material can occur for permanently anchoring said lens system within the eye.

2. The lens system of claim 1 including temporary attachment means for locating said lens system with respect to the pupillary aperture of the iris until tissue growth into the fibrous material is accomplished.

3. The lens system of claim 2 wherein said temporary attachment means is at least one hook formed of a biologically absorbable filament.

4. The lens system of claim 2 including at least one integral, laterally projecting loop for mounting through the pupillary aperture of the iris and effective to hold said optical lens portion and said haptical portion in contact with the anterior surface of the iris so that tissue growth into said fibrous material can occur.

5. The lens system of claim 1 wherein:
   said fibrous material is comprised of Dacron polyester.

6. The lens system of claim 2 wherein said temporary attachment means is a circular loop attached to said lens portion by at least two axially extending and parallel pins, with said loop being mounted coaxially with and parallel to the plane of said optical lens portion.

7. An artificial intraocular lens system adapted to be implanted within a living eye immediately adjacent the iris of the eye and comprising:
   a plastic optical lens portion formed with at least one integral, laterally projecting loop adapted to be mounted through the pupillary aperture of the iris and effective when mounted to contact one surface of the iris; and
   a sleeve of biologically tolerable fibrous material mounted on the outer periphery of said loop and into which tissue of the iris can grow so as to anchor the lens portion within the eye.

* * * * *